United States Patent
Weinstein et al.

(10) Patent No.: US 9,788,752 B2
(45) Date of Patent: Oct. 17, 2017

(54) IMPLANTABLE DIELECTROMETER

(71) Applicant: Kyma Medical Technologies Ltd., Tel Aviv (IL)

(72) Inventors: Uriel Weinstein, Mazkeret Batia (IL); Assaf Bernstein, Givat Nili (IL); Eyal Cohen, Gedera (IL); Dov Oppenheim, Jerusalem (IL); Moshe Mosesko, Kadima (IL)

(73) Assignee: ZOLL MEDICAL ISRAEL LTD., Kfar Sabba (IL)

( * ) Notice: Subject to any disclaimer, the term of this patent is extended or adjusted under 35 U.S.C. 154(b) by 0 days.

(21) Appl. No.: 14/948,238

(22) Filed: Nov. 20, 2015

(65) Prior Publication Data

US 2016/0073924 A1    Mar. 17, 2016

Related U.S. Application Data

(63) Continuation of application No. 13/811,217, filed as application No. PCT/IB2011/053246 on Jul. 21, 2011, now Pat. No. 9,220,420.
(Continued)

(51) Int. Cl.
*A61B 5/00* (2006.01)
*A61B 5/053* (2006.01)
(Continued)

(52) U.S. Cl.
CPC ............ *A61B 5/0538* (2013.01); *A61B 1/313* (2013.01); *A61B 5/0028* (2013.01);
(Continued)

(58) Field of Classification Search
CPC ..... A61B 5/053; A61B 5/0538; A61B 5/0205; A61B 5/0028; A61B 5/0031;
(Continued)

(56) References Cited

U.S. PATENT DOCUMENTS 4,240,445 A * 12/1980 Iskander et al. .............. 607/156
4,344,440 A *  8/1982 Aaby et al. ................... 600/430
(Continued)

FOREIGN PATENT DOCUMENTS

DE        10008886      9/2001
EP        1834588 A1    9/2007
(Continued)

OTHER PUBLICATIONS

Haude et al., Intracoronary Doppler—and Quantitative Coronary Angiography-Derived Predictors of Major Adverse Cardiac Eve2009/152625nts After Stent Implantation, Mar. 6, 2011, Circulation, vol. 103(9), pp. 1212-1217.
(Continued)

*Primary Examiner* — Max Hindenburg
(74) *Attorney, Agent, or Firm* — Cooley LLP

(57) ABSTRACT

Diagnostic apparatus (24) includes a sealed case (80), comprising a biocompatible material and configured for implantation within a body of a human subject (22). A dielectrometric probe (26, 50, 63, 66, 70, 102, 160) is connected to the case and includes first and second conductors (40, 42, 54, 56, 64, 67, 68, 72, 74, 162, 164), which are configured to be placed in proximity to a target tissue (34) in the body. A driving circuit (82), which is contained in the case, is coupled to apply a radio-frequency (RF) signal to the probe and to sense the signal returned from the probe. Processing circuitry (84) is configured to evaluate, responsively to the returned signal, a dielectric property of the target tissue.

19 Claims, 8 Drawing Sheets

Related U.S. Application Data

(60) Provisional application No. 61/366,173, filed on Jul. 21, 2010.

(51) Int. Cl.

| | | |
|---|---|---|
| *A61B 5/05* | (2006.01) | |
| *A61N 1/375* | (2006.01) | |
| *A61B 5/0205* | (2006.01) | |
| *A61B 1/313* | (2006.01) | |
| *A61B 5/07* | (2006.01) | |
| *A61B 5/08* | (2006.01) | |
| *A61B 17/34* | (2006.01) | |
| *A61B 5/01* | (2006.01) | |
| *A61B 5/0215* | (2006.01) | |
| *A61B 5/042* | (2006.01) | |
| *A61B 5/145* | (2006.01) | |
| *A61N 1/365* | (2006.01) | |
| *A61N 1/37* | (2006.01) | |
| *A61N 1/372* | (2006.01) | |

(52) U.S. Cl.
CPC .......... *A61B 5/0031* (2013.01); *A61B 5/0059* (2013.01); *A61B 5/0205* (2013.01); *A61B 5/05* (2013.01); *A61B 5/0537* (2013.01); *A61B 5/076* (2013.01); *A61B 5/0809* (2013.01); *A61B 5/416* (2013.01); *A61B 5/4244* (2013.01); *A61B 5/4552* (2013.01); *A61B 5/4875* (2013.01); *A61B 5/686* (2013.01); *A61B 5/6833* (2013.01); *A61B 5/72* (2013.01); *A61B 17/3468* (2013.01); *A61N 1/3756* (2013.01); *A61B 5/01* (2013.01); *A61B 5/0215* (2013.01); *A61B 5/0422* (2013.01); *A61B 5/14542* (2013.01); *A61B 2560/0219* (2013.01); *A61B 2562/0214* (2013.01); *A61B 2562/164* (2013.01); *A61N 1/36521* (2013.01); *A61N 1/3702* (2013.01); *A61N 1/37229* (2013.01)

(58) Field of Classification Search
CPC ........ A61B 2017/00026; A61B 5/0537; A61B 5/6833; A61B 5/686; A61B 5/0809; A61B 5/416; A61B 5/4244; A61B 5/4552; A61B 5/076; A61B 5/72; A61B 2562/0214; A61B 2562/164; A61B 17/3468
See application file for complete search history.

(56) References Cited

U.S. PATENT DOCUMENTS

| | | | |
|---|---|---|---|
| 4,557,272 A | 12/1985 | Carr | |
| 4,632,128 A | 12/1986 | Paglione et al. | |
| 4,640,280 A | 2/1987 | Sterzer | |
| 4,641,659 A | 2/1987 | Sepponen | |
| 4,774,961 A | 10/1988 | Carr | |
| 4,825,880 A | 5/1989 | Stauffer et al. | |
| 4,926,868 A | 5/1990 | Larsen | |
| 4,958,638 A | 9/1990 | Sharpe | |
| 4,986,870 A | 1/1991 | Frohlich | |
| 5,003,622 A | 3/1991 | Ma et al. | |
| 5,109,855 A | 5/1992 | Guner | |
| 5,394,882 A | 3/1995 | Mawhinney | |
| 5,404,877 A | 4/1995 | Nolan | |
| 5,540,727 A | 7/1996 | Tockman et al. | |
| 5,549,650 A | 8/1996 | Bornzin et al. | |
| 5,668,555 A | 9/1997 | Starr | |
| 5,704,355 A | 1/1998 | Bridges | |
| 5,766,208 A | 6/1998 | McEwan | |
| 5,807,257 A | 9/1998 | Bridges | |
| 5,829,437 A | 11/1998 | Bridges | |
| 5,865,177 A | 2/1999 | Segawa | |
| 5,967,986 A | 10/1999 | Cimochowski et al. | |
| 6,019,724 A | 2/2000 | Gronningsaeter et al. | |
| 6,061,589 A | 5/2000 | Bridges et al. | |
| 6,064,903 A | 5/2000 | Riechers et al. | |
| 6,093,141 A | 7/2000 | Mosseri et al. | |
| 6,144,344 A | 11/2000 | Kim | |
| 6,193,669 B1 | 2/2001 | Degany et al. | |
| 6,208,286 B1 | 3/2001 | Rostislavovich et al. | |
| 6,233,479 B1 | 5/2001 | Haddad et al. | |
| 6,330,479 B1 | 12/2001 | Stauffer | |
| 6,454,711 B1 | 9/2002 | Haddad et al. | |
| 6,480,733 B1 | 11/2002 | Turcott | |
| 6,526,318 B1 | 2/2003 | Ansarinia | |
| 6,592,518 B2 | 7/2003 | Denker et al. | |
| 6,604,404 B2 | 8/2003 | Paltieli et al. | |
| 6,729,336 B2 | 5/2004 | Da Silva et al. | |
| 6,730,033 B2 | 5/2004 | Yao et al. | |
| 6,755,856 B2 | 6/2004 | Fierens et al. | |
| 6,933,811 B2 * | 8/2005 | Enokihara et al. ........... 333/202 | |
| 6,940,457 B2 | 9/2005 | Lee et al. | |
| 7,020,508 B2 | 3/2006 | Stivoric et al. | |
| 7,122,012 B2 | 10/2006 | Bouton et al. | |
| 7,130,681 B2 | 10/2006 | Gebhardt et al. | |
| 7,184,824 B2 * | 2/2007 | Hashimshony ...... A61B 5/0507 | |
| | | | 600/547 |
| 7,191,000 B2 | 3/2007 | Zhu et al. | |
| 7,197,356 B2 | 3/2007 | Carr | |
| 7,266,407 B2 | 9/2007 | Li et al. | |
| 7,267,651 B2 | 9/2007 | Nelson | |
| 7,272,431 B2 | 9/2007 | McGrath | |
| 7,280,863 B2 | 10/2007 | Shachar | |
| 7,454,242 B2 | 11/2008 | Fear et al. | |
| 7,474,918 B2 | 1/2009 | Frants et al. | |
| 7,479,790 B2 | 1/2009 | Choi | |
| 7,493,154 B2 | 2/2009 | Bonner et al. | |
| 7,529,398 B2 | 5/2009 | Zwirn et al. | |
| 7,570,063 B2 | 8/2009 | Van Veen et al. | |
| 7,591,792 B2 | 9/2009 | Bouton | |
| 7,697,972 B2 | 4/2010 | Verard et al. | |
| 7,719,280 B2 | 5/2010 | Lagae et al. | |
| 7,747,302 B2 | 6/2010 | Milledge et al. | |
| 7,868,627 B2 | 1/2011 | Turkovskyi | |
| 8,032,211 B2 | 10/2011 | Hashimshony et al. | |
| 8,295,920 B2 | 10/2012 | Bouton et al. | |
| 8,352,015 B2 | 1/2013 | Bernstein et al. | |
| 8,473,054 B2 | 6/2013 | Pillai et al. | |
| 8,882,759 B2 * | 11/2014 | Manley ............. A61B 18/1815 | |
| | | | 606/34 |
| 8,938,292 B2 | 1/2015 | Hettrick et al. | |
| 8,983,592 B2 | 3/2015 | Belalcazar | |
| 9,220,420 B2 * | 12/2015 | Weinstein et al. | |
| 2002/0032386 A1 | 3/2002 | Sackner et al. | |
| 2002/0045836 A1 | 4/2002 | Alkawwas | |
| 2002/0049394 A1 | 4/2002 | Roy et al. | |
| 2002/0050954 A1 | 5/2002 | Jeong-Kun et al. | |
| 2002/0147405 A1 | 10/2002 | Denker et al. | |
| 2003/0036713 A1 | 2/2003 | Bouton et al. | |
| 2003/0088180 A1 | 5/2003 | Van Veen et al. | |
| 2003/0100815 A1 | 5/2003 | Da Silva et al. | |
| 2003/0219598 A1 | 11/2003 | Sakurai | |
| 2004/0015087 A1 | 1/2004 | Boric-Lubecke et al. | |
| 2004/0073081 A1 | 4/2004 | Schramm | |
| 2004/0077952 A1 | 4/2004 | Rafter et al. | |
| 2004/0249257 A1 | 12/2004 | Tupin et al. | |
| 2004/0254457 A1 | 12/2004 | van der Weide | |
| 2004/0261721 A1 | 12/2004 | Steger | |
| 2005/0038503 A1 | 2/2005 | Greenhalgh et al. | |
| 2005/0107693 A1 | 5/2005 | Fear et al. | |
| 2005/0245816 A1 | 11/2005 | Candidus et al. | |
| 2006/0004269 A9 | 1/2006 | Caduff et al. | |
| 2006/0009813 A1 | 1/2006 | Taylor et al. | |
| 2006/0025661 A1 | 2/2006 | Sweeney et al. | |
| 2006/0265034 A1 | 11/2006 | Aknine et al. | |
| 2007/0016032 A1 | 1/2007 | Aknine | |
| 2007/0016050 A1 | 1/2007 | Moehring et al. | |
| 2007/0100385 A1 | 5/2007 | Rawat | |
| 2007/0123770 A1 | 5/2007 | Bouton et al. | |
| 2007/0135721 A1 | 6/2007 | Zdeblick | |
| 2007/0152812 A1 | 7/2007 | Wong et al. | |

(56) References Cited

U.S. PATENT DOCUMENTS

| | | |
|---|---|---|
| 2007/0191733 A1 | 8/2007 | Gianchandani et al. |
| 2007/0263907 A1 | 11/2007 | McMakin et al. |
| 2008/0027313 A1 | 1/2008 | Shachar |
| 2008/0030284 A1 | 2/2008 | Tanaka et al. |
| 2008/0036668 A1 | 2/2008 | White et al. |
| 2008/0097199 A1 | 4/2008 | Mullen |
| 2008/0129511 A1 | 6/2008 | Yuen et al. |
| 2008/0167566 A1 | 7/2008 | Unver et al. |
| 2008/0169961 A1 | 7/2008 | Steinway et al. |
| 2008/0183247 A1 | 7/2008 | Harding |
| 2008/0200802 A1 | 8/2008 | Bahavaraju et al. |
| 2008/0224688 A1 | 9/2008 | Rubinsky et al. |
| 2008/0269589 A1 | 10/2008 | Thijs et al. |
| 2008/0283282 A1 | 11/2008 | Kawasaki et al. |
| 2008/0294036 A1 | 11/2008 | Hoi et al. |
| 2008/0316124 A1 | 12/2008 | Hook |
| 2009/0048500 A1 | 2/2009 | Corn |
| 2009/0076350 A1 | 3/2009 | Bly et al. |
| 2009/0153412 A1 | 6/2009 | Chiang et al. |
| 2009/0187109 A1 | 7/2009 | Hashimshony |
| 2009/0203972 A1 | 8/2009 | Heneghan et al. |
| 2009/0227882 A1 | 9/2009 | Foo |
| 2009/0240132 A1 | 9/2009 | Friedman |
| 2009/0240133 A1 | 9/2009 | Friedman |
| 2009/0248450 A1 | 10/2009 | Fernandez |
| 2009/0281412 A1 | 11/2009 | Boyden et al. |
| 2009/0299175 A1 | 12/2009 | Bernstein et al. |
| 2009/0312615 A1 | 12/2009 | Caduff et al. |
| 2009/0322636 A1 | 12/2009 | Brigham et al. |
| 2010/0056907 A1 | 3/2010 | Rappaport et al. |
| 2010/0081895 A1 | 4/2010 | Zand |
| 2010/0106223 A1 | 4/2010 | Grevious |
| 2010/0256462 A1 | 10/2010 | Rappaport et al. |
| 2010/0265159 A1 | 10/2010 | Ando et al. |
| 2010/0312301 A1 | 12/2010 | Stahmann |
| 2010/0321253 A1 | 12/2010 | Vazquez et al. |
| 2011/0004076 A1 | 1/2011 | Janna et al. |
| 2011/0022325 A1 | 1/2011 | Craddock et al. |
| 2011/0060215 A1 | 3/2011 | Tupin et al. |
| 2011/0068995 A1 | 3/2011 | Baliarda et al. |
| 2011/0130800 A1 | 6/2011 | Weinstein et al. |
| 2012/0029323 A1 | 2/2012 | Zhao |
| 2012/0098706 A1 | 4/2012 | Lin et al. |
| 2012/0104103 A1 | 5/2012 | Manzi |

FOREIGN PATENT DOCUMENTS

| | | |
|---|---|---|
| JP | 10-137193 A | 5/1998 |
| JP | 2000-235006 A | 8/2000 |
| JP | 2001-525925 A | 12/2001 |
| JP | 2004-526488 A | 9/2004 |
| JP | 2006-208070 A | 8/2006 |
| JP | 2007-061359 A | 3/2007 |
| JP | 2008-515548 A | 5/2008 |
| JP | 2008-518706 A | 6/2008 |
| JP | 2008-530546 A | 7/2008 |
| JP | 2008-542759 A | 11/2008 |
| JP | 2009-514619 | 4/2009 |
| JP | 2009-522034 A | 6/2009 |
| JP | 2010-512190 A | 4/2010 |
| JP | 2011-524213 A | 9/2011 |
| WO | WO2006/127719 | 11/2006 |
| WO | WO 2006/130798 A2 | 12/2006 |
| WO | WO 2007/017861 A2 | 2/2007 |
| WO | WO2008/070856 | 6/2008 |
| WO | WO2008/148040 | 12/2008 |
| WO | WO 2009/031149 A2 | 3/2009 |
| WO | WO2009/031150 | 3/2009 |
| WO | WO 2009/060182 A1 | 5/2009 |
| WO | WO 2009/152625 | 12/2009 |
| WO | WO2009/152625 A1 | 12/2009 |
| WO | WO 2011/067623 A1 | 6/2011 |
| WO | WO 2011/141915 A2 | 11/2011 |

OTHER PUBLICATIONS

Beyer-Enke et al., Intra-arterial Doppler flowmetry in the superficial femoral artery following angioplasty., 2000, European Radiology, vol. 10, No. 4, pp. 642-649.

Ringer et al., Follow-up of Stented Carotid Arteries by Doppler Ultrasound, Sep. 2002, Neurosurgery, vol. 51, No. 3, pp. 639-643.

Kantarci et al., Follow-up of Extracranial Vertebral Artery Stents with Doppler Sonography., Sep. 2006, American Journal of Roentgenology, vol. 187, pp. 779,787.

Ghosh, et al., Immediate Evaluation of Angioplasty and Stenting Results in Supra-Aortic Arteries by Use of a Doppler-Tipped Guidewire, Aug. 2004, American Journal of Neuroradiology, vol. 25, pp. 1172-1176.

International Search Report and Written Opinion, dated Nov. 26, 2013 for Application No. PCT/IB2013/00663 filed Feb. 15, 2013.

International Patent Application PCT/IB2009/055438, "Locating Features in the Heart Using Radio Frequency Imaging", Filed on Dec. 1, 2009.

International Application PCT/IB2009/055438 Search Report dated Jul. 20, 2010.

International Application PCT/IB2010/054861 Search Report dated Apr. 5, 2011.

Ascension Technology Corporation, "TrakSTAR Adds Versatility to Ascension's New Product Line: Desktop Model Joins driveBAY Tracker for Fast Guidance of Miniaturized Sensor", USA, Apr. 7, 2008.

Claron Technology Inc., "MicronTracker 3:A New Generation of Optical Trackers", Canada, 2009.

Immersion Corporation, "Immersion Introduces New 3D Digitizing Product-MicroScribe G2; Faster Data Transfer, USB Compatibility, New Industrial Design", Press Release, San Jose, USA, Jul. 1, 2002.

Polhemus, "Fastrak: The Fast and Easy Digital Tracker", USA, 2008.

Czum et al., "The Vascular Diagnostic Laboratory", The Heart & Vascular Institute Newsletter, vol. 1, USA, Winter, 2001.

Lal et al., "Duplex ultrasound velocity criteria for the stented carotid artery", Journal of Vascular Surgery, vol. 47, No. 1, pp. 63-73, Jan. 2008.

Larsson et al., "State Diagrams of the Heart—a New Approach to Describing Cardiac Mechanics", Cardiovascular Utrasound 7:22 (2009).

Bell et al., "A Low-Profile Achimedean Spiral Antenna Using an EBG Ground Plane", IEEE Antennas and Wireless Propagation Letters 3, pp. 223-226 (2004).

Supplementary European Search Report for Application No. EP 10834292.4 (PCT/IB2010/054861) dated Dec. 4, 2014.

Lin, J.C. et al., "Microwave Imaging of Cerebral Edema", Proceedings of the IEEE, IEEE, NY, US, vol. 70, No. 5; May 1, 1982, pp. 523.524.

Guido Biffi Gentili et al., "A Versatile Microwave Plethysmograph for the Monitoring of Physiological Parameters", IEEE Transactions on Biomedical Engineering, IEEE Service Center, Pitscataway, NJ, US, vol. 49, No. 10, Oct. 1, 2002.

Pedersen P C et al., "Microwave Reflection and Transmission Measurements for Pulmonary Diagnosis and Monitoring", IEEE Transactions on Biomedical Engineering, IEEE Service Center, Piscataway, NJ, US, vol. BME-25, No. 1, Jan. 1, 1978; pp. 40-48.

Extended Search Report for European Application No. 11809360.8 dated Mar. 11, 2014.

International Search Report for International Application No. PCT/IB2011/053246 dated Dec. 13, 2011.

Miura et al., "Time Domain Reflectometry: Measurement of Free Water in Normal Lung and Pulmonary Edema," *American Journal of Physiology— Lung Physiology* 276:1 (1999), pp. L207-L212.

Liang, Jing et al., Microstrip Patch Antennas on Tunable Electromagnetic Band-Gap Substrates, IEEE Transactions on Antennas and Propagation, vol. 57, No. 6, Jun. 2009.

Yang, F. et al. "Enhancement of Printed Dipole Antennas Characteristics Using Semi-EBG Ground Plane", Journal of Electromagnetic Waves and Application, U.S., Taylor & Francis, Apr. 3, 2006, vol. 8, pp. 993-1006.

(56) References Cited

OTHER PUBLICATIONS

International Search Report and Written Opinion of the International Searching Authority, dated Dec. 2, 2011, for International Application No. PCT/IB2011/053244.
International Preliminary Report on Patentability, dated Jan. 31, 2013, for International Application No. PCT/IB2011/053244.
International Preliminary Report on Patentability, dated Jan. 31, 2013, for International Application No. PCT/IB2011/053246.
Supplementary European Search Report and European Search Opinion, dated Feb. 26, 2014, for European Application No. 11809359.

* cited by examiner

IMPLANTABLE DIELECTROMETER

CROSS-REFERENCE TO RELATED APPLICATION

This application is a continuation of U.S. patent application Ser. No. 13/811,217, filed Mar. 28, 2013, titled "Implantable Dielectrometer," which in turn is a 35 U.S.C. 371 national stage entry of PCT/IB2011/053246, which has an international filing date of Jul. 21, 2011 and entitled "Implantable Dielectrometer," and claims the benefit of U.S. Provisional Patent Application 61/366,173, filed Jul. 21, 2010. The present application incorporates herein by reference the disclosure of each of the above-referenced applications in their entireties.

FIELD OF THE INVENTION

The present invention relates generally to methods and systems for medical diagnostic measurement and monitoring, and specifically to measuring dielectric properties of physiological tissue.

BACKGROUND OF THE INVENTION

The permittivity $\in$ of a physical medium is the relationship between the electric displacement field D and the electric field E in the material: $D = \in E$. The permittivity of a homogeneous material is commonly expressed relative to the permittivity of free space, $\in_0$, in terms of the relative permittivity, $\in_r$, defined by $\in = \in_0 \in_r$. The relative permittivity is also referred to as the "dielectric constant" of the material. The permittivity of a lossy material (such as physiological tissue) can be defined as a complex, frequency-dependent function:

$$\hat{\varepsilon} = \varepsilon' - j\varepsilon'' = \varepsilon' - j\frac{\sigma}{\omega\varepsilon_0},$$

wherein $\in'$ is the real part of the permittivity, $\sigma$ is the conductivity of the material, and $\omega$ is the frequency, while $\in_0$ is the free space permittivity.

Dielectrometers are used to measure dielectric properties, such as the permittivity, of materials. For example, U.S. Pat. No. 7,479,790 describes a capacitive plate dielectrometer, in which a small sample of a test material is inserted inside a capacitor for measurement of its dielectric properties. As another example, U.S. Pat. No. 7,868,627 describes a method for measuring dielectric characteristic of material by irradiating the material with a microwave signal and detecting the reflected signal.

SUMMARY

Embodiments of the present invention that are described hereinbelow provide implantable devices for measuring dielectric properties of body tissues. These devices are useful, inter alia, in monitoring fluid levels within body organs.

There is therefore provided, in accordance with an embodiment of the present invention, diagnostic apparatus, which include a sealed case, including a biocompatible material and configured for implantation within a body of a human subject. A dielectrometric probe is connected to the case and includes first and second conductors, which are configured to be placed in proximity to a target tissue in the body. A driving circuit is contained in the case and is coupled to apply a radio-frequency (RF) signal to the probe and to sense the signal returned from the probe. Processing circuitry is configured to evaluate, responsively to the returned signal, a dielectric property of the target tissue.

Typically, the driving circuit is configured to apply the RF signal to the probe and to sense the returned signal at multiple different frequencies.

In some embodiments, the dielectric property evaluated by the processing circuitry includes a complex permittivity of the target tissue. The processing circuitry may be configured to evaluate the complex permittivity by measuring an impedance between the first and second conductors. Alternatively or additionally, the processing circuitry may be configured to evaluate the complex permittivity by measuring a reflection of the signal from the probe, which is indicative of an impedance mismatch at the target tissue. Further alternatively or additionally, the processing circuitry may be configured to evaluate the complex permittivity by measuring a delay of the signal transmitted through the probe. In one embodiment, the processing circuitry is configured to evaluate the complex permittivity by measuring a resonant frequency of the probe.

In a disclosed embodiment, the conductors are arranged to provide a coaxial contact to the target tissue at a distal end of the probe. The coaxial contact may include a patch, which is configured to be placed against the target tissue. Alternatively, the coaxial contact may include a coaxial tip, in which the first conductor is concentrically contained within the second conductor, wherein the tip is configured for insertion into the target tissue.

In other embodiments, the conductors are arranged to define a transmission line in proximity to the target tissue. The transmission line may be defined by arranging the first conductor as a ground plane and the second conductor as a microstrip parallel to the ground plane. Alternatively, the transmission line may be defined by arranging the first and second conductors as parallel lines. Further alternatively, the transmission line may include a coplanar waveguide.

In another embodiment, the conductors are arranged to define a resonant ring in proximity to the target tissue.

In some embodiments, the processing circuitry is configured to derive a measure of a fluid content of the target tissue from the dielectric property. The processing circuitry may be configured to measure the fluid content continuously or intermittently, and may be configured to measure changes in the fluid content over time.

In disclosed embodiments, the case is configured for implantation in a thorax of the subject, and the target tissue includes a lung of the subject. The probe may be configured for insertion between a rib cage and pleura of the subject and may be configured to bend freely in one direction, while resisting bending in any other direction. The case may be configured for insertion between a pair of ribs of the subject.

In some of these embodiments, the apparatus includes a tool configured to be inserted between ribs of the subject and to guide insertion of the probe into the rib cage. The tool may include an optical channel, which is configured to be placed alongside the probe during the insertion of the probe into the rib cage and to enable an operator of the tool to view an area into which the probe is to be inserted.

In alternative embodiments, the target tissue is spleen, liver, tongue or palate tissue.

In a disclosed embodiment, at least a part of the processing circuitry is contained in the case and is configured to convey information via a wireless link to a telemetry station outside the body. Alternatively or additionally, the processing circuitry is configured to communicate with at least one other implanted device.

In some embodiments, the apparatus includes a power antenna, which is configured to receive electrical energy to power the processing circuitry via an inductive link from a transmitter outside the body.

The apparatus may further include one or more additional sensors, which are connected to the case and are configured for implantation in the body. At least one of the additional sensors may include an electrode, which is configured to receive electrical signals from the heart, wherein the processing circuitry is configured to gate a measurement of the returned signal responsively to the electrical signals from the heart.

Additionally or alternatively, the processing circuitry may be configured to detect a modulation of the dielectric property due to at least one of a heartbeat and a respiratory motion of the subject.

There is also provided, in accordance with an embodiment of the present invention, a diagnostic method, which includes implanting a dielectrometric probe, including first and second conductors, in proximity to a target tissue in a body of a human subject. A radio-frequency (RF) signal is applied to the probe, and a dielectric property of the target tissue is evaluated responsively to the signal returned from the probe.

The present invention will be more fully understood from the following detailed description of the embodiments thereof, taken together with the drawings in which:

DETAILED DESCRIPTION OF EMBODIMENTS

Overview

Figure 1:
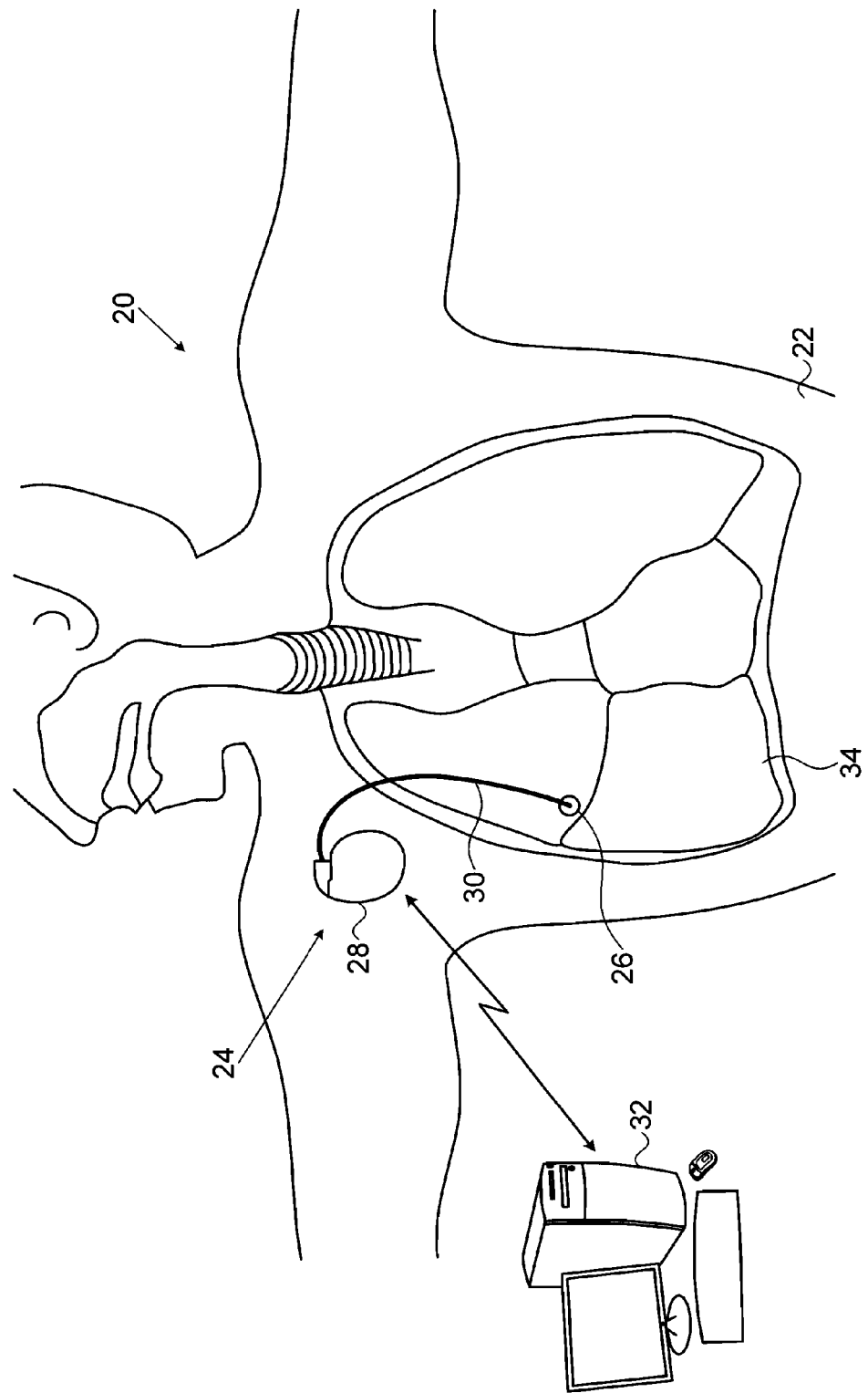
FIG. 1 is a schematic pictorial illustration showing a monitoring system including an implanted dielectrometric monitoring device, in accordance with an embodiment of the invention.

A number of chronic medical conditions lead to accumulation of fluid in and around body organs. One such condition is pulmonary edema, which is associated with chronic heart failure and other pathologies. Other conditions can lead to fluid accumulation in other organs, such as the liver, spleen, tongue, palate, and splanchnic system. Monitoring fluid levels in the patient's body over extended periods can be helpful in ongoing risk assessment and adjustment of treatment.

The dielectric properties of body tissues vary due to changes in physiological conditions and are particularly sensitive to fluid accumulation in the tissues. For example, the relative permittivity of normal lung tissue (in the UHF frequency range) varies from 20 to 40 between inhalation and exhalation. In pulmonary edema, however, the relative permittivity increases due to water content in the lungs, and may reach 75 in serious cases. Thus, monitoring the dielectric properties of body tissues can provide a useful diagnostic indicator with respect to pulmonary edema and other conditions that are associated with fluid buildup.

Embodiments of the present invention that are described hereinbelow provide such diagnostic monitoring functions by means of an implantable dielectrometric device. The device comprises a sealed case, comprising a biocompatible material, which is implanted in the body of a human subject. The case is connected to or contains a dielectrometric probe, comprising a pair of conductors, which are placed in proximity to a target tissue, such as the lung. The term "proximity," in the context of the present patent application and in the claims, means that the target tissue is close enough to the distal end of the probe to have a significant impact on the impedance between the conductors. "Proximity" in the context of the embodiments described below is generally limited to a distance of not more than 1-2 cm from the target tissue.

A driving circuit in the sealed case applies a radio-frequency (RF) signal to the probe and senses the signal returned from the probe in order to measure the impedance between the conductors. This impedance will vary as a function of the dielectric properties of the target tissue, including the permittivity and conductivity, which together define the complex permittivity of the tissue. The driving circuit typically applies the RF signal to the probe at multiple different frequencies, so that the complex permittivity is measured as a function of frequency. A processing circuit may then evaluate the dielectric properties of the target tissue based on the measured impedance. Following the impedance calculation over frequency, a water content assumption can be estimated based on multi-material liquid model with the respective permittivity over different frequencies.

In a general material including loss and permittivity, impedance is defined as follows:

$$\eta = \frac{j\omega\mu}{\gamma} \quad (1)$$

Here $\omega$ is the radial frequency, and $\mu$ is the material permeability (which in the case of a biological tissue is equal to the free space permeability $\mu=\mu_0$). $\gamma$ is the complex propagation constant which is defined as follows:

$$\gamma = j\omega\sqrt{\mu\varepsilon_0}\sqrt{\varepsilon' - j\varepsilon''} \quad (2)$$

In this equation, $c_0$ is the free-space electromagnetic propagation velocity, and $\in'$ and $\in''$ are the real and imaginary part of the complex permittivity. As noted earlier, the imaginary part of the complex permittivity is related to the conductivity:

$$\in'' = \sigma/\omega\in_0. \quad (3)$$

The above expressions are thus used to relate the measured impedance, as a function of frequency, to the complex permittivity.

The impedance between the conductors due to the target tissue can be measured in a number of ways. In some embodiments, the driving circuit measures the reflection of the signal from the probe, which is indicative of an impedance mismatch at the target tissue at the end of the probe. In other embodiments, the driving circuit measures the delay of the signal transmitted through the probe, which is indicative of the permittivity of the target tissue. In other embodiments, the driving circuit measures a resonating frequency of a printed resonator (such as a ring or other shaped circuit), which is indicative of the properties of tissues in its proximity. Various probe configurations that may be used for these types of measurements are described hereinbelow.

The embodiments that are shown in the figures and are described below are directed to devices that are implanted in the thorax for purposes of monitoring fluid levels in the lungs. Alternatively, the principles of the present invention may similarly be applied in other monitoring applications. For example, implanted devices of the types described herein may be used, mutatis mutandis, in monitoring pericardial fluid levels. In other embodiments, such devices may be used in long-term monitoring of fluid levels in the brain, spleen, tongue, palate or liver, as well as in body extremities, such as the thighs. More generally, the devices and methods described herein may be adapted for use in substantially any long-term diagnostic application in which measuring the dielectric properties of tissue is of value, including not only fluid monitoring but also imaging applications, as well.

System Description and Probe Configurations

Figure 8:
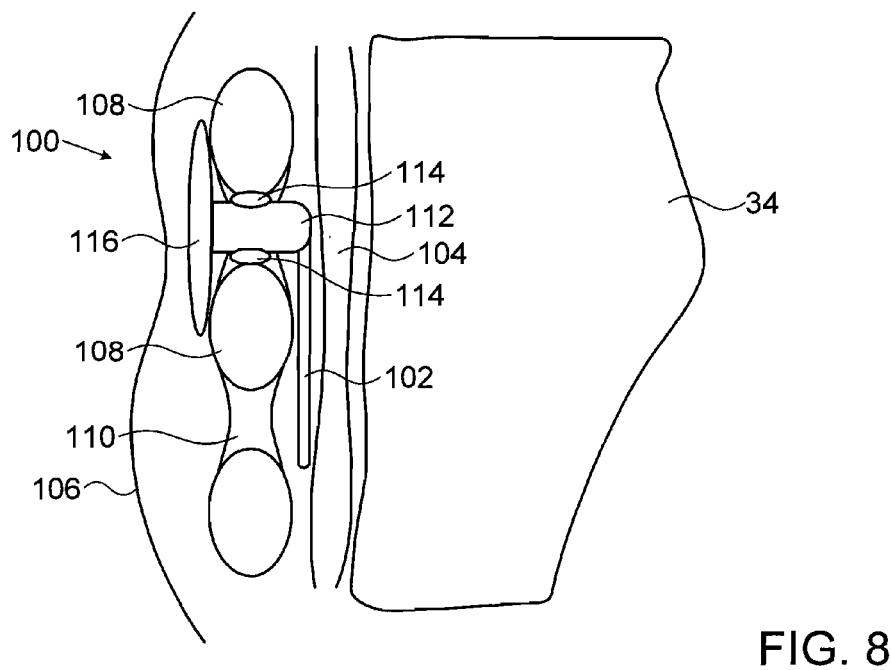
FIG. 8 is a schematic, sectional view through the thorax of a human subject, showing implantation of a dielectrometric monitoring device in the thorax, in accordance with an embodiment of the invention.
Figure 9:
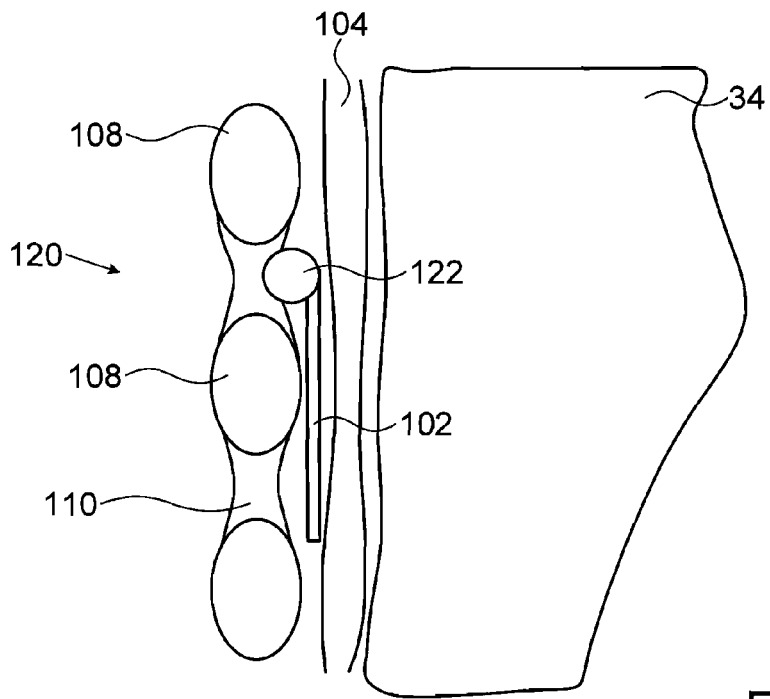
FIG. 9 is a schematic, sectional view through the thorax of a human subject, showing implantation of a dielectrometric monitoring device in the thorax, in accordance with another embodiment of the invention.

FIG. 1 is a schematic pictorial illustration showing a monitoring system 20 including a dielectrometric monitoring device 24 implanted in the thorax of a patient 22, in accordance with an embodiment of the invention. Device 24 comprises an electronic unit 28, which is typically similar in shape and size to a conventional implanted cardiac device (ICD), such as a pacemaker, and is implanted below the patient's skin using a minimally-invasive procedure. (In an alternative embodiment, device 24 may also include electrodes and be configured to pace the patient's heart, in addition to the diagnostic functions that are described herein.) Device 24 may alternatively be implanted in other locations, as shown in FIGS. 8 and 9, for example.

Electronic unit 28 is connected to a probe 26 by a cable 30. Probe 26 is positioned in or alongside a lung 34 of patient 22. Device 24 drives the probe via the cable with RF signals, typically including multiple signals at different frequencies within a chosen range, such as the microwave range. Optionally, the frequency range may be even wider, from 100 MHz to 2.5 GHz, for example, or even from a few kHz up to several GHz, depending on the desired resolution, depth and permittivity range of the measurements. The circuits in unit 28 measure the impedance of the probe in response to the signals, which depends on the dielectric properties (permittivity and conductivity) of the lung tissue that is in proximity to the probe.

Based on the measured impedance, device 24 derives an indication of the dielectric properties of the tissue in lung 34. These dielectric properties are themselves indicative of physiological conditions of the tissue, such as fluid content. Device 24 collects these indications over time and periodically transmits the data to a telemetry station 32, typically via a suitable short-range wireless link. Alternatively or additionally, device 24 may transmit the raw impedance measurements to station 32, which then processes the measurements itself to extract the dielectric properties and physiological conditions of the tissue.

Station 32 typically comprises a general-purpose computer with suitable communication circuits and software, and may be located in a clinic or hospital or in the home or workplace of patient 22. Station 32 may also be configured to program device 24 over the wireless link, as well as to provide RF energy to recharge the battery in device 24, as described below. Station 32 may also comprise a gateway, relaying information between device 24 and a server across a network, as well as serving as the user interface for the device. Such a gateway may be, for example, a desktop station or a smart-phone.

Figure 2:
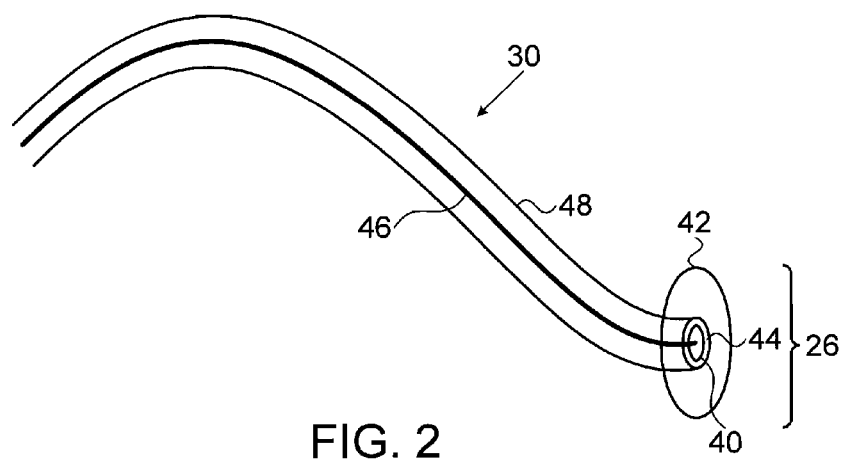
FIG. 2 is a schematic pictorial view of a dielectrometric probe, in accordance with an embodiment of the invention.

FIG. 2 is a schematic pictorial view of dielectrometric probe 26, in accordance with an embodiment of the invention. Cable 30 comprises a pair of conductors 46, 48, arranged coaxially. The conductors terminate in this embodiment in an open-coax patch arrangement, in which conductor 46 connects to a central electrode 40, and conductor 48 connects to a ring electrode 42 surrounding electrode 40. Electrodes 40 and 42 are separated by a non-conductive ring 44. Probe 26 may comprise, for example, a flexible or rigid circuit substrate (not shown), made from a biocompatible material, on which electrodes 40 and 42 are printed or otherwise deposited. Although probe 26 is shown in this figure as being oriented perpendicular to coaxial cable 30, in other embodiments, the probe may be oriented parallel to the cable.

The impedance between conductors 46 and 48 within cable 30 is fixed, but the impedance between electrodes 40 and 42 at the termination of the conductors will vary as a function of the complex permittivity of the tissue in proximity to probe 26. RF signals transmitted down cable 30 to probe 26 will be reflected back from the probe due to the mismatch between the cable impedance and the impedance encountered by the probe due to the tissue permittivity. The amplitude and phase of the reflected signal at any given frequency will depend on the impedance encountered by the probe at that frequency. Device 24 analyzes the amplitude and phase of the reflected signals over a range of frequencies in order to derive a measure of the complex impedance.

Figure 3:
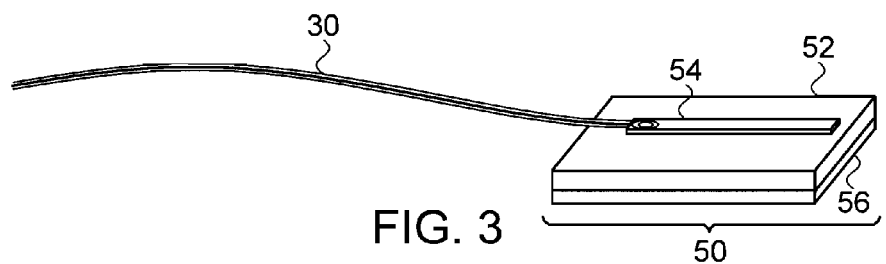
FIG. 3 is a schematic pictorial view of a dielectrometric probe, in accordance with another embodiment of the invention.

FIG. 3 is a schematic pictorial view of a dielectrometric probe 50, in accordance with another embodiment of the invention. Probe 50 may be used with device 24 in place of probe 26 in the system configuration that is shown in FIG. 1. Alternatively, probe 50 may be mounted directly on the electronic unit of a dielectrometric device, which is then implanted itself in proximity to the target tissue. In this latter alternative embodiment (not shown in the figures), cable 30 is not needed.

In the embodiment of FIG. 3, probe 50 is configured as a microstrip transmission line. One of the conductors in cable 30 connects to a ground plane 56 on one side of a circuit substrate 52. The other conductor connects to a microstrip 54 on the opposite side of substrate 52. The complex permittivity of the tissue in proximity to microstrip 54 changes the effective permittivity of the transmission line at its cross section, thus changing its characteristic impedance and velocity factor. These impedance and velocity factors affect both the amplitude and the propagation delay of the signals passing through the transmission line in probe 50 and cable 30. Either or both of these properties may be measured in order to assess the impedance and thus estimate the permittivity of the target tissue. To measure the propagation delay, both ends of microstrip 54 may be connected by conductors to the driver circuits in device 24, rather than only one end as in the pictured embodiment.

Figure 4A:
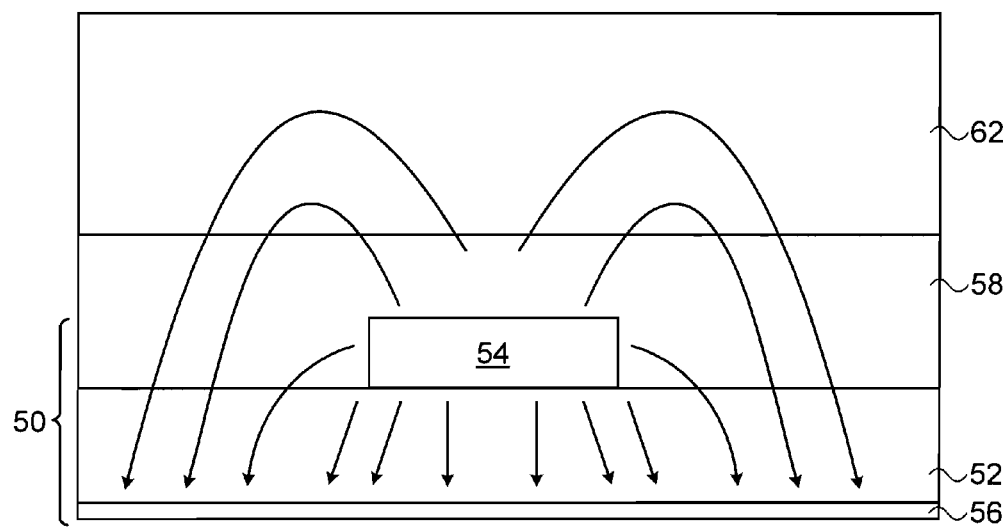
FIG. 4A is a schematic sectional view of the probe of FIG. 3, showing lines of an electric field generated by the probe, in accordance with an embodiment of the invention.

FIG. 4A is a schematic sectional view of probe 50, showing lines of the electric field emitted from the probe, in accordance with an embodiment of the invention. Although this figure shows a particular stripline-type transmission line configuration, the principles of this embodiment apply equally to other sorts of transmission lines, such as a coplanar waveguide, grounded coplanar waveguide, parallel lines, as shown in the figures that follow, or any other transmission line configuration.

The lines of field emitted from microstrip 54 in FIG. 4A pass through intermediate tissue 58, with which probe 50 is in contact (such as the pleura), into target tissue 62 (such as the lung). Changes in the dielectric properties of target tissue 62 will affect the field lines and consequently the impedance of the transmission line. The cross-sectional configuration of probe 50 is optimized to achieve wide spreading of the electric and magnetic fields, in order to increase the sensitivity of the probe to dielectric changes in tissue 62. Generally speaking, the configuration is chosen so that the electromagnetic flux is denser at the deeper targeted measurement volume. The probe is thus able to sense dielectric change at larger distances. For measuring lung fluid content, probe 50 is typically 1-2 cm wide and a few millimeters thick.

Figure 4B:
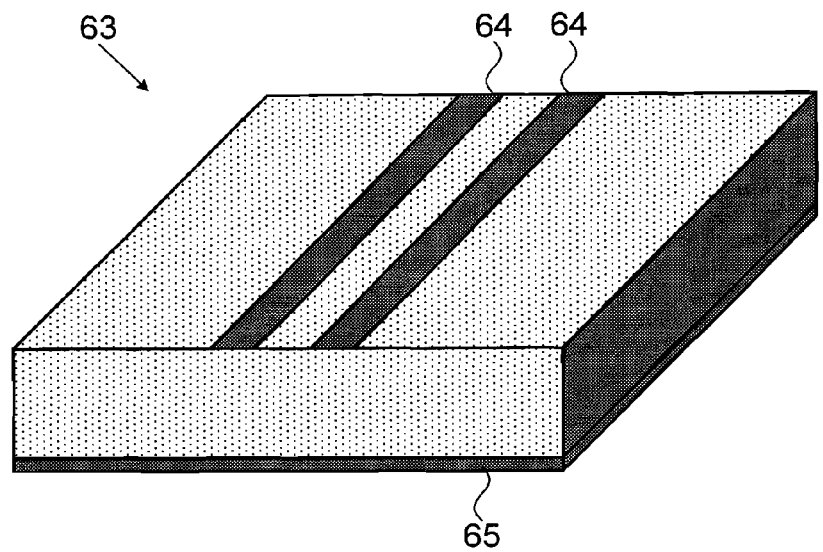
FIGS. 4B and 4C are schematic pictorial views of dielectrometric probes, in accordance with alternative embodiments of the present invention.
Figure 4C:
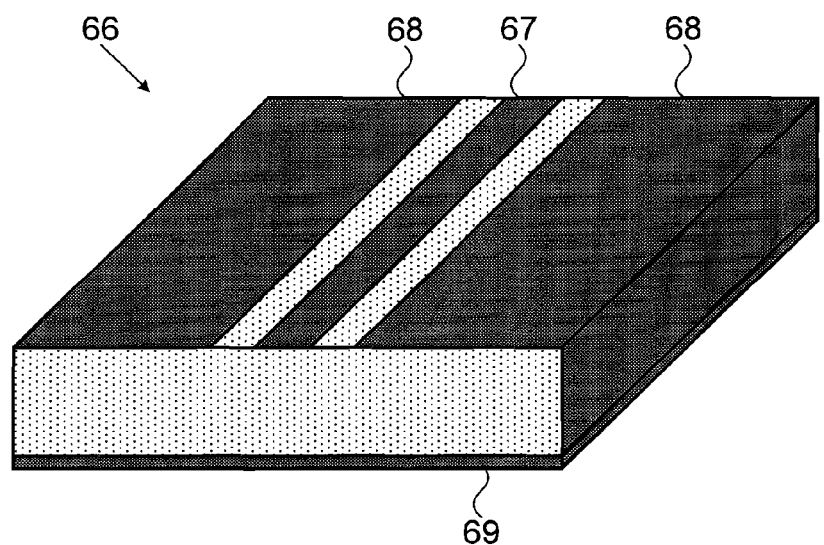

FIGS. 4B and 4C are schematic pictorial views of dielectrometric probes 63 and 66, in accordance with alternative embodiments of the present invention. Probe 63 comprises two parallel conducting lines 64 formed on one side of a substrate, with a ground plane 65 formed on the other. Probe 66 is a grounded coplanar waveguide, with a conductive strip 67 between coplanar ground planes 68 on one side of a substrate and a ground plane 69 on the other.

Figure 5:
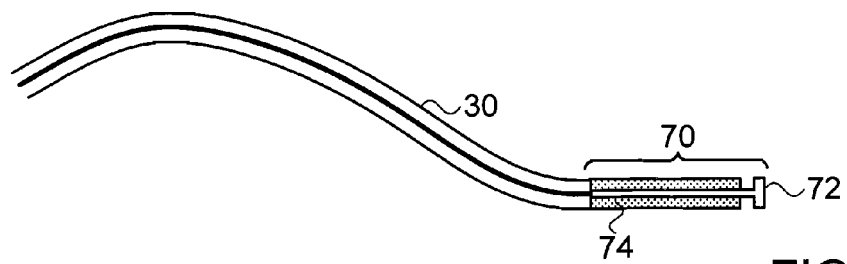
FIG. 5 is a schematic side view of a dielectrometric probe, in accordance with yet another embodiment of the invention.

Elimination of ground plane 69 would make probe 66 a simple coplanar waveguide. FIG. 5 is a schematic side view of a dielectrometric probe 70, in accordance with yet another embodiment of the invention. Probe 70 may also be used with device 24 in place of probe 26 in system 20. Probe 70 comprises a coaxial tip at the end of cable 30, in which a central conductor 72 is concentrically contained within a peripheral conductive cylinder 74. Central conductor 72 protrudes from surrounding cylinder 74 and can even be inserted into the target tissue. This geometry enables impedance measurement deeper into the tissue. Contact between the tip and the tissue causes an impedance mismatch with cable 30, leading to reflections that can be used to measure complex permittivity as in the preceding embodiments.

Signal Processing

Figure 6:
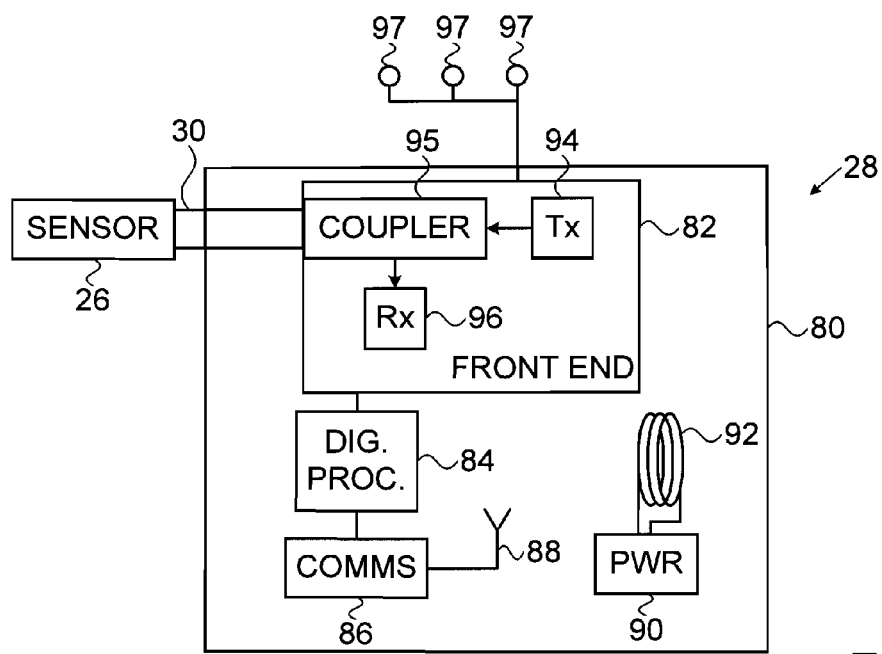
FIG. 6 is a block diagram that schematically shows functional components of a dielectrometric monitoring device, in accordance with an embodiment of the invention.

FIG. 6 is a block diagram that schematically shows functional components of dielectrometric monitoring device 24, in accordance with an embodiment of the invention. The elements of electronic unit 28 are contained in a sealed case 80 comprising a suitable biocompatible material, such as titanium or stainless steel. Case 80 contains, inter alia, circuitry including a front end driver circuit 82 and a digital processing circuit 84. Driver circuit 82 comprises a transmitter 94, which transmits RF signals via a directional coupler 95 or bridge through cable 30 to probe 26 (or to one of the other probes described above). A receiver 96 in the driver circuit receives the signals that are returned from probe 26 via cable 30 and outputs a digitized indication of the amplitude and phase of the signals to digital processing circuit 84. Typically, the driver circuit applies the signals at multiple, different frequencies, and uses frequency-tuned detection in sensing the returned signal at each frequency.

Processing circuit 84 samples the input signals transmitted by driver circuit 82, and uses the sampled input as an amplitude and phase reference. The processing circuit then compares the digitized signals received from the driver circuit to the reference in order to calculate the amplitude and phase shift of the returned signals. Based on the amplitude and phase shifts and/or the propagation delay of the received signal relative to the transmitted signal, taken as a function of frequency over the range of frequencies transmitted by the driver circuit, processing circuit 84 derives the complex impedance between the conductors of the probe due to the target tissue. The processing circuit (or station 32, FIG. 1) evaluates the permittivity of the target tissue based on these measurements.

The circuits of device 24 measure the permittivity in order to compute an indication of the fluid content of lung 34. These measurements may be made continuously, or they may be made periodically and/or on command. Typically, digital processing circuit 84 comprises a memory (not shown), which stores the computed values. Circuit 84 may perform statistical analyses on the recorded values over time, such as computing trends and changes. Circuit 84 may issue an alarm if the fluid content rises above a predetermined threshold level.

To determine the permittivity, processing circuit 84 may transform the frequency-domain measurements of the returned signals to the time domain, filter the time-domain signals to remove spurious reflections due to impedance discontinuities along the line to probe 26, and then transform the filtered signals back to the frequency domain. Circuit 84 may derive the load admittance Ymeas of the probe from the measured signals using the following formula:

$$Ymeas = \sigma + jB = Y_0 \frac{1 - \Gamma meas}{1 + \Gamma meas} \tag{4}$$

Here Γmeas is the measured reflection coefficient in the frequency domain, and Yo is the characteristic admittance of the transmission line. The load admittance is composed of a parallel conductance σ and a susceptance B. The susceptance reflects the edge capacitance of the probe, which in turn is related to the permittivity of the tissue.

Incorporating the capacitance and conductance functions into equation (4) and matching with the measured admittance gives the expression:

$$Ymeas/Y_0 = j\omega C_1 Z_0 + j\omega' \in Z_0 + Z_0 \sigma \qquad (5)$$

wherein $Z_0$ is the characteristic impedance of the measurement transmission line. A non-linear solver can be applied to the admittance values given in equation (4) to extract the conductance and capacitance of the tissue. The complex permittivity is the found using equations (1)-(3) above. The real permittivity is related to $\in_2$, while the imaginary permittivity is related to both the frequency and the conductivity.

The water content of the tissue may be derived from the measured permittivity using empirical calibration curves or other techniques that are known in the art. Techniques that may be used for this purpose are described, for example, by Miura et al., in "Time Domain Reflectometry: Measurement of Free Water in Normal Lung and Pulmonary Edema," *American Journal of Physiology—Lung Physiology* 276:1 (1999), pages L207-L212, which is incorporated herein by reference.

Device 24 may optionally comprise additional sensors 97, connected to electronic unit 28. Sensors 97 may comprise, for example, one or more electrodes, which sense electrical activity of the heart. The resulting signals can be used to gate the measurements of dielectric properties of the tissue. Additionally or alternatively, sensors 97 may comprise a posture or motion sensor, such as an accelerometer. Posture in particular has an effect on fluid distribution within the lungs, and processing circuit 84 may use the posture measurement in refining its assessment of fluid content. Further additionally or alternatively, processing circuit may detect a modulation of the dielectric properties due to the heartbeat and/or respiratory motion of the subject.

A communication interface 86 transmits and receives data to and from telemetry station 32 (FIG. 1) via a communication antenna 88. The transmitted data typically comprise the indications of permittivity and/or tissue fluid content that have been computed over time and stored by digital processing circuit 84. Alternatively or additionally, circuit 84 may transmit raw data regarding the returned signals and/or impedance for further processing in the telemetry station. Further alternatively or additionally, communication interface 86 may transmit data continuously as they are measured.

A power source 90 supplies operating power to the circuits of device 24. Power source 90 typically comprises an energy storage component, such as a single-use or rechargeable battery. In the case of a rechargeable storage component, power source 90 may be coupled to a power antenna 92, which receives RF power from a suitable power transmission antenna (not shown) outside the body. Such a transmission antenna may comprise, for example, a coil, which is positioned outside the body of patient 22 in proximity to device 24 and provides power to antenna 92 by magnetic induction. The power transmission coil may be placed under a mattress on which the patient lies, or it may be worn as a vest, a bra or a necklace, for example. Power source 90 rectifies the received power in order to charge its energy storage component.

Figure 7A:
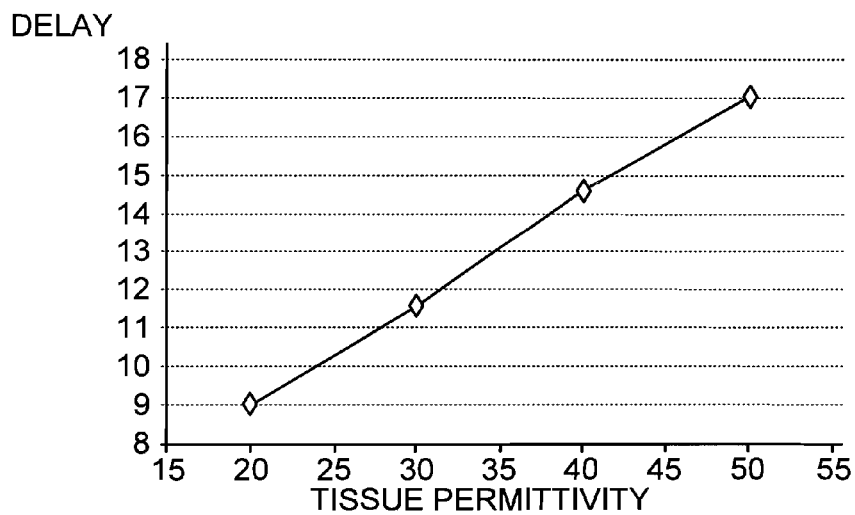
FIG. 7A is a plot showing the relationship between tissue permittivity and signal delay measured by a dielectrometric monitoring device, in accordance with an embodiment of the invention.

FIG. 7A is a plot showing the relationship between tissue permittivity and signal delay measured by dielectrometric monitoring device 24, in accordance with an embodiment of the invention. This plot is based on a simulation of the performance of a transmission line-type probe, such as probe 50 (FIGS. 3-4). The permittivity of the tissue in the simulation is varied between 20 and 50, and the delay through the line is calculated and normalized in terms of nanoseconds per meter of length. There is a clear linear relation between the measured phase and the evaluated permittivity.

The delay thus provides a reliable measure of tissue permittivity. In addition, as the permittivity changes, there will also be an amplitude change in the returned signals due to impedance mismatch and ohmic losses. Each probe used in system 20 may be pre-calibrated in order to find the exact relation between delay and/or amplitude of the returned wave and the tissue permittivity, and the resulting calibration factors may then be programmed into processing circuit 84.

Figure 7B:
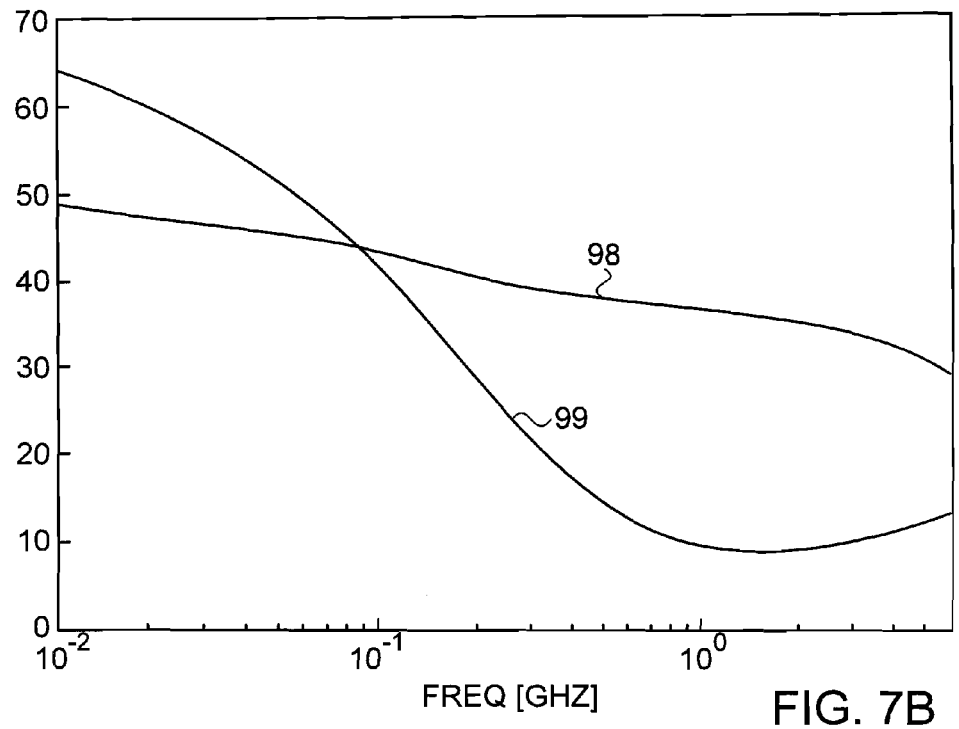
FIG. 7B is a plot of the complex permittivity of lung tissue as a function of frequency, in accordance with an embodiment of the present invention.

FIG. 7B is a plot of the complex permittivity of lung tissue as a function of frequency, in accordance with an embodiment of the present invention. The real and imaginary parts of the permittivity are shown by respective curves 98 and 99. These permittivity values were derived from experimental results using the relations expressed by equations (4) and (5) above.

Alternative Implant Locations and Implantation Techniques

FIG. 8 is a schematic, sectional view through the thorax of a human subject, showing implantation of a dielectrometric monitoring device 100 in the thorax, in accordance with an embodiment of the invention. To implant device 100, the surgeon makes a small incision through skin 106 and through muscle 110 between ribs 108. A probe 102 is then threaded, through the incision, into the rib cage, so that the probe is positioned outside pleura 104 of lung 34, and an electronics unit 112 is connected to the probe. Typically, unit 112 is placed between two of the lower ribs at the side of the thorax. Tissue-growth inducing materials 114 may be applied around unit 112 in order to facilitate tissue integration of the device. Electronic unit 112 and a thin, circular coil 116 are left outside ribs 108. Coil 116 enables charging of device 100, as described above. Unit 112 is attached to the ribs using standard attachment methods.

FIG. 9 is a schematic, sectional view through the thorax of a human subject, showing implantation of a dielectrometric monitoring device 120 in the thorax, in accordance with another embodiment of the invention. In this case, an electronic unit 122 of device 120 is made small enough to allow internal placement, inside the rib cage.

Figure 10:
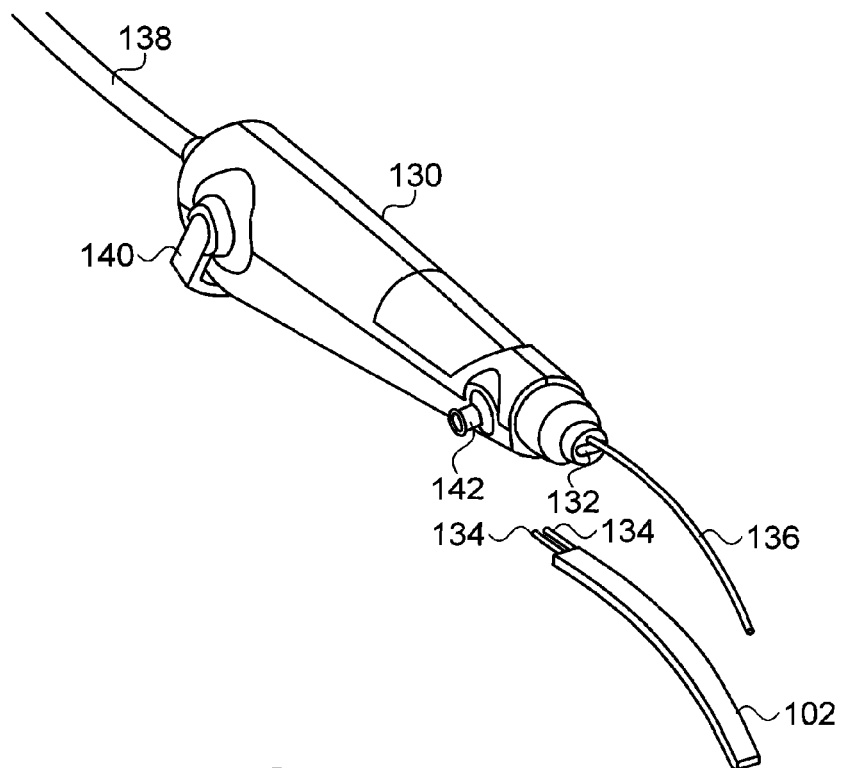
FIG. 10 is a schematic pictorial illustration of a surgical tool for use in implantation of a dielectrometric probe, in accordance with an embodiment of the present invention.

FIG. 10 is a schematic pictorial illustration of a surgical tool 130 for use in implantation of dielectrometric probe 102, in accordance with an embodiment of the present invention. Tool 130 comprises a receptacle 132 at its distal end, into which end terminals 134 of probe 102 are inserted. (After probe 102 has been implanted and properly positioned using tool 130, receptacle 132 is disengaged from terminals 134, which are then connected to electronics unit 112.) For ease of implantation, probe 102 may be internally reinforced so as to bend freely in only one direction (the downward direction in FIG. 10), while resisting bending in any other direction.

Tool 130 comprises an optical channel 136, such as a fiberoptic bundle, which runs along the upper surface of probe 102 when the probe is connected to receptacle 132. Channel 136 connects to an image sensor and a light source (not shown in the figures) inside tool 130, which in turn connect via a cable 138 to a console (not shown). The surgeon implanting probe 102 is thus able to view the area between and behind ribs 108 during implantation. A navigation knob 140 enables the surgeon to move channel 136 up and down, and possibly to move probe 102 along with it. A fluid connection allows water to be introduced to rinse channel 136.

Figure 11:
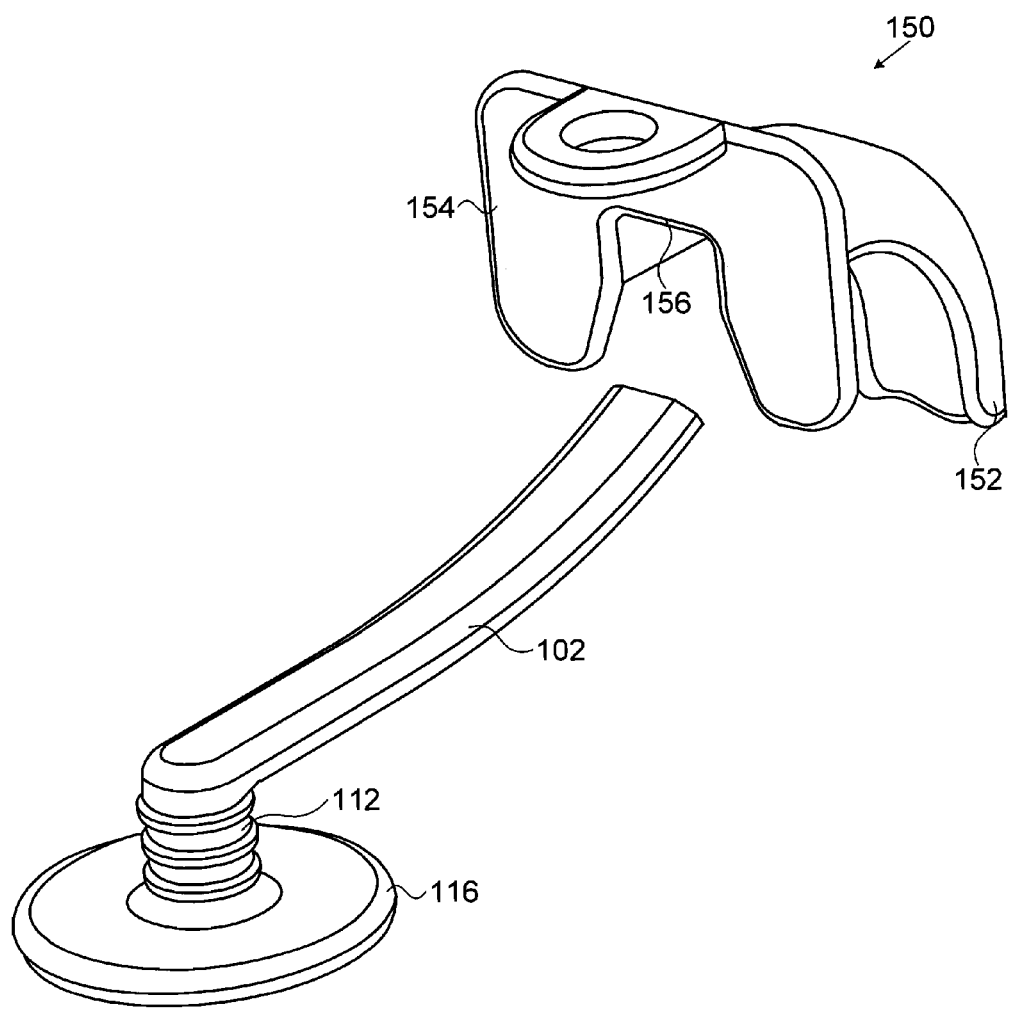
FIG. 11 is a schematic pictorial illustration showing a dielectrometric probe and a surgical accessory for use in implantation of the probe, in accordance with an embodiment of the present invention.

FIG. 11 is a schematic pictorial illustration showing a surgical accessory 150 for use in implantation of probe 102, in accordance with an embodiment of the present invention. The surgeon inserts a distal tip 152 of accessory 150 between ribs 108, thus defining an entry path for probe 102 (with or without the use of tool 130). A stopper 154 limits the depth of insertion of tip 152 and thus prevents unnecessary trauma to the patient. After inserting accessory 150 between the ribs, the surgeon threads the distal end of probe 102 through an opening 156, and tip 152 then guides the distal end downward to the desired position adjacent to pleura 104. The accessory is then removed, and probe 102 is affixed to its location, for example by sewing it to the rib or muscle or connective tissue surrounding the ribs.

Resonant Probe

Figure 12:
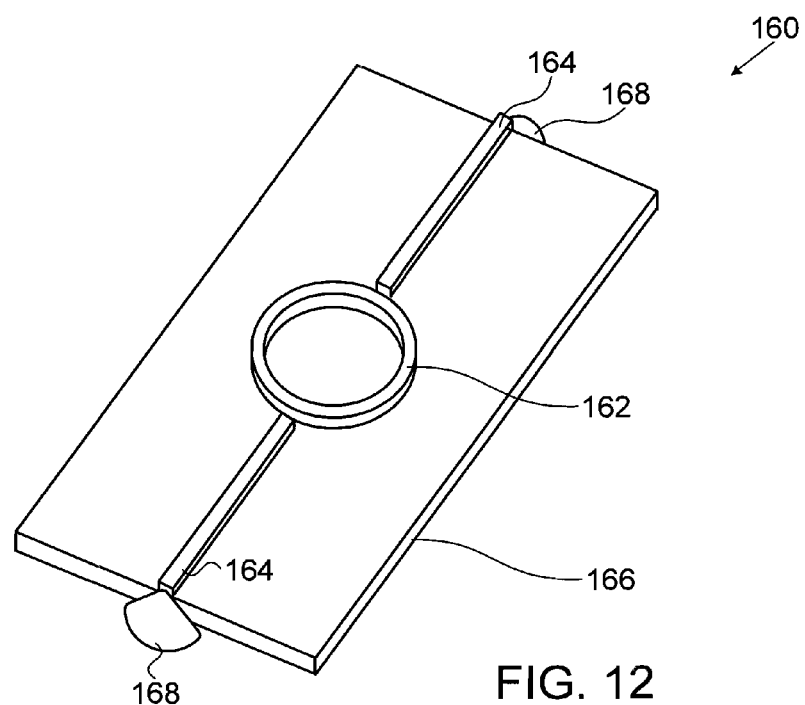
FIG. 12 is a schematic top view of a dielectrometric probe, in accordance with a further embodiment of the present invention.

FIG. 12 is a schematic top view of a dielectrometric probe 160, in accordance with a further embodiment of the present invention. Probe 160 comprises a conductive ring 162, which is printed on a substrate 166. Conductors 164 on substrate 166 link ring 162 to ports 168, with small gaps between the conductors and the ring to isolate the ring for the purpose of resonance measurements.

When ring 162 is excited by an electromagnetic wave transmitted between ports 168, a standing wave is created in the ring. The points of maximum and minimum voltage in the standing wave depend on the propagation velocity in the ring, which in turn depends on the permittivity of the tissue in proximity to the ring. The ring will have a number of resonant frequencies (in first- and higher-order modes), which depend on the tissue permittivity. The size and other parameters of ring 162 are chosen so that the resonant frequencies depend on the permittivity at a particular depth within the tissue. The excitation frequency of probe 160 is scanned over a range of frequencies in order to find the resonant frequency of ring 162 and thus measure the tissue permittivity.

Figure 13:
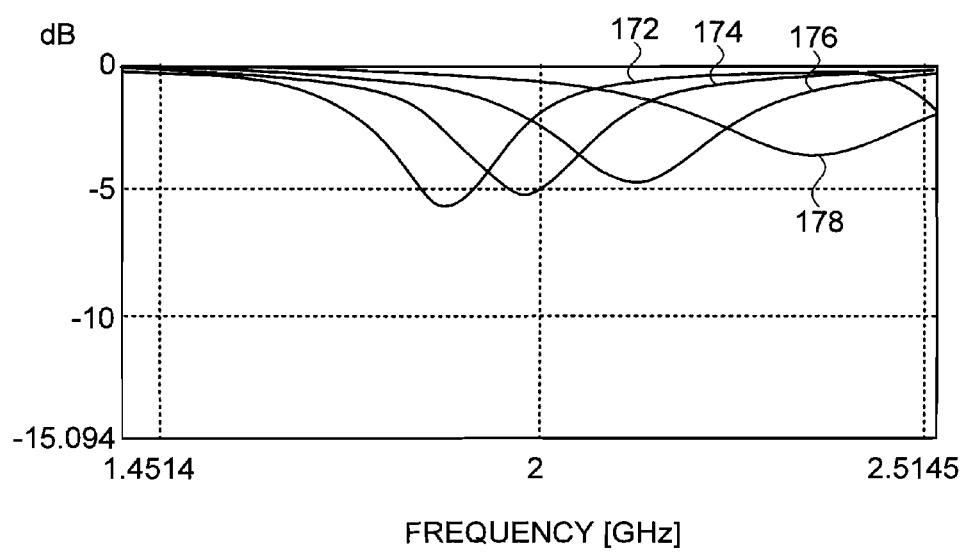
FIG. 13 is a plot showing the frequency response of the probe of FIG. 12 for different values of tissue permittivity, in accordance with an embodiment of the present invention.

FIG. 13 is a plot showing the frequency response of probe 160 for different values of the tissue permittivity, in accordance with an embodiment of the present invention. The vertical axis of the plot corresponds to the reflection coefficient of the probe, which drops by 3-5 dB at the resonant frequency. Curves 172, 174, 176 and 178 show the coefficient as a function of frequency for tissue permittivity values of 20, 30, 40 and 50, respectively. The resonance frequency shifts over a range of about 500 MHz. By measuring this frequency shift, probe 160 thus provides an accurate measure of the tissue permittivity, and hence of the fluid level.

In an alternative embodiment (not shown in the figures), a dielectrometric probe is placed near the diaphragm and has sensing flaps, which make it possible to measure not only lung fluids, but also liver fluids (to the right) or spleen fluids (to the left). The dielectrometric device and probe can be designed to permit multiple different measurements of this sort to be made, even simultaneously. Although the embodiments shown in the figures relate specifically to measurement of the fluid content of the lungs, the principles of the present invention may similarly be applied in monitoring of other organs, such as the heart, bladder, spleen, liver, tongue, palate, brain, and body extremities.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A diagnostic method, comprising:
    implanting a dielectrometer probe, comprising first and second conductors, in proximity to a target tissue in a body of a human subject;
    applying a radio-frequency (RF) signal to the probe; and
    evaluating, responsively to a signal from the probe, a dielectric property of the target tissue including finding a complex permittivity of the target tissue,
    wherein finding the complex permittivity of the target tissue includes one of:
        measuring a reflection of the signal from the probe, which is indicative of an impedance mismatch at the target tissue;
        measuring a delay of the signal transmitted through the probe; and
        measuring a resonant frequency of the probe.

2. The method according to claim 1, wherein applying the RF signal comprises applying RF signals and sensing returned signals at multiple different frequencies.

3. The method according to claim 1, wherein finding the complex permittivity further includes measuring an impedance between the first and second conductors.

4. A diagnostic method, comprising:
    implanting a dielectrometer probe, comprising first and second conductors, in proximity to a target tissue in a body of a human subject;
    applying a radio-frequency (RF) signal to the probe; and
    evaluating, responsively to a signal from the probe, a dielectric property of the target tissue;
    wherein the first and second conductors are arranged to:
        provide a coaxial contact to the target tissue at a distal end of the probe, or
        define a resonant ring in proximity to the target tissue.

5. The method according to claim 4, wherein the first and second conductors are arranged to provide a coaxial contact to the target tissue at a distal end of the probe, and the coaxial contact comprises a patch, which is placed against the target tissue.

6. The method according to claim 4, wherein the first and second conductors are arranged to provide a coaxial contact to the target tissue at a distal end of the probe, and the coaxial contact comprises a coaxial tip, in which the first conductor is concentrically contained within the second conductor, wherein the tip is inserted into the target tissue.

7. A diagnostic method, comprising:
    implanting a dielectrometer probe, comprising first and second conductors, in proximity to a target tissue in a body of a human subject; the first and second conductors arranged to define a transmission line in proximity to the target tissue;
    applying a radio-frequency (RF) signal to the probe; and
    evaluating, responsively to a signal from the probe, a dielectric property of the target tissue; wherein:

the transmission line is defined by arranging the first conductor as a ground plane and the second conductor as a microstrip parallel to the ground plane; or the transmission line comprises a coplanar waveguide.

8. The method according to claim 4, wherein the first and second conductors are arranged to define a transmission line in proximity to the target tissue and the transmission line is defined by arranging the first and second conductors as parallel lines.

9. The method according to claim 1, further comprising deriving a measure of a fluid content of the target tissue from the dielectric property.

10. The method according to claim 9, wherein deriving the measure comprises measuring the fluid content continuously.

11. The method according to claim 9, wherein deriving the measure comprises measuring the fluid content intermittently.

12. The method according to claim 9, wherein deriving the measure comprises measuring changes in the fluid content over time.

13. The method according to claim 1, further comprising implanting a case, which is connected to the probe, in a thorax of the subject.

14. The method according to claim 4, further comprising deriving a measure of a fluid content of the target tissue from the dielectric property.

15. The method according to claim 14, wherein deriving the measure comprises measuring changes in the fluid content over time.

16. The method according to claim 4, wherein applying the RF signal comprises applying RF signals and sensing returned signals at multiple different frequencies.

17. The method according to claim 7, further comprising deriving a measure of a fluid content of the target tissue from the dielectric property.

18. The method according to claim 14, wherein deriving the measure comprises measuring changes in the fluid content over time.

19. The method according to claim 7, wherein applying the RF signal comprises applying RF signals and sensing returned signals at multiple different frequencies.

* * * * *